US 10,864,231 B2

(12) United States Patent
Willoughby et al.

(10) Patent No.: US 10,864,231 B2
(45) Date of Patent: Dec. 15, 2020

(54) BOTULINUM TOXIN AND COLLOIDAL SILVER PARTICLES

(71) Applicants: Andrew J. M. Willoughby, Langley (CA); AMERICAN SILVER, LLC, American Fork, UT (US); DR. ANDREW WILLOUGHBY INC., Langley (CA)

(72) Inventors: Andrew J. M. Willoughby, Langley (CA); Keith William Moeller, Highland, UT (US)

(73) Assignees: American Silver, LLC, American Fork, UT (US); Dr. Andrew Willoughby Inc., Vancouver (CA)

( * ) Notice: Subject to any disclaimer, the term of this patent is extended or adjusted under 35 U.S.C. 154(b) by 0 days.

(21) Appl. No.: 15/508,096

(22) PCT Filed: Aug. 28, 2015

(86) PCT No.: PCT/US2015/047601
§ 371 (c)(1),
(2) Date: Mar. 1, 2017

(87) PCT Pub. No.: WO2016/036618
PCT Pub. Date: Mar. 10, 2016

(65) Prior Publication Data
US 2017/0281678 A1 Oct. 5, 2017

Related U.S. Application Data

(60) Provisional application No. 62/044,926, filed on Sep. 2, 2014.

(51) Int. Cl.
A61K 33/38 (2006.01)
A61K 8/04 (2006.01)
A61K 9/19 (2006.01)
A61K 47/02 (2006.01)
A61K 9/00 (2006.01)
A61K 9/10 (2006.01)
A61K 8/64 (2006.01)
A61Q 19/08 (2006.01)
A61K 8/19 (2006.01)
A61K 8/66 (2006.01)
A61K 38/48 (2006.01)

(52) U.S. Cl.
CPC ............. A61K 33/38 (2013.01); A61K 8/042 (2013.01); A61K 8/044 (2013.01); A61K 8/19 (2013.01); A61K 8/64 (2013.01); A61K 8/66 (2013.01); A61K 9/0019 (2013.01); A61K 9/10 (2013.01); A61K 9/19 (2013.01); A61K 38/4893 (2013.01); A61K 47/02 (2013.01); A61Q 19/08 (2013.01); A61K 2800/41 (2013.01); A61K 2800/413 (2013.01); A61K 2800/882 (2013.01); A61K 2800/91 (2013.01)

(58) Field of Classification Search
CPC .... A61K 33/38; A61K 38/4893; A61K 8/044; A61P 17/00; A61P 31/00
See application file for complete search history.

(56) References Cited

U.S. PATENT DOCUMENTS

| 6,214,299 | B1 | 4/2001 | Holladay et al. | |
|---|---|---|---|---|
| 6,447,787 | B1* | 9/2002 | Gassner | A61K 31/335 424/236.1 |
| 6,720,006 | B2* | 4/2004 | Hanke | A01N 59/16 424/400 |
| 6,743,348 | B2 | 6/2004 | Holladay et al. | |
| 7,135,195 | B2 | 11/2006 | Holladay et al. | |
| 8,318,181 | B2 | 11/2012 | Edelson et al. | |
| 8,535,728 | B2 | 9/2013 | Holladay et al. | |
| 2007/0059255 | A1* | 3/2007 | Tichy | A61L 2/0088 424/48 |
| 2007/0190174 | A1* | 8/2007 | Holladay | A61K 33/38 424/618 |
| 2010/0055138 | A1* | 3/2010 | Margulies | A61K 8/02 424/401 |
| 2010/0168023 | A1* | 7/2010 | Ruegg | A61K 8/64 514/8.9 |
| 2010/0187091 | A1 | 7/2010 | Pierce et al. | |
| 2011/0262556 | A1 | 10/2011 | Holladay et al. | |
| 2011/0293681 | A1* | 12/2011 | Berlin | A61L 15/46 424/405 |
| 2012/0064136 | A1 | 3/2012 | Baker et al. | |
| 2014/0086900 | A1 | 3/2014 | Jung et al. | |
| 2014/0099342 | A1 | 4/2014 | Edelson et al. | |

FOREIGN PATENT DOCUMENTS

| WO | 20000015245 A1 | 3/2000 |
|---|---|---|
| WO | 2008079898 | 7/2008 |
| WO | 2008079898 A1 | 7/2008 |
| WO | 2009009143 | 1/2009 |
| WO | 2012048854 | 4/2012 |

OTHER PUBLICATIONS

International Search Report and Written Opinion for PCT/US2015/047601 dated Dec. 4, 2015.

* cited by examiner

Primary Examiner — Mina Haghighatian
(74) Attorney, Agent, or Firm — BioMed IP

(57) ABSTRACT

Botulinum toxin is combined with colloidal silver particles to provide improved compositions for use in medical and cosmetic treatments.

5 Claims, No Drawings

BOTULINUM TOXIN AND COLLOIDAL SILVER PARTICLES

CROSS-REFERENCE TO RELATED APPLICATION

This application is a national phase application under 35 U.S.C. § 371 of International Application No. PCT/US2015/047601, filed Aug. 28, 2016, which claims the benefit under 35 U.S.C. § 119(e) of U.S. Provisional Patent Application No. 62/044,926 filed Sep. 2, 2014, each application is incorporated herein by reference in its entirety.

FIELD OF THE INVENTION

The present invention relates generally to botulinum toxin in combination with colloidal silver particles for medical and cosmetic purposes.

BACKGROUND

In the 1950's, scientists discovered that botulinum toxin can reduce muscle spasms. In the 1960's and 1970's, studies were performed to explore botulinum toxin as a treatment for strabismus (crossed eyes). In 1989, Allergan Inc. Irvine, Calif., USA introduced BOTOX®, the first botulinum toxin approved by the FDA to treat blepharospasm (eyelid spasms) and strabismus. In 2000, the FDA approved BOTOX® therapy for cervical dystonia to reduce the severity of abnormal head position and neck pain. In 2002, the FDA approved BOTOX® Cosmetic (onabotulinumtoxin A), the same formulation as BOTOX®, with dosing specific to moderate to severe frown lines between the brow. In 2004, the FDA approved BOTOX® for severe underarm sweating when topical medicines don't work well enough. Several other preparations of botulinum toxin are now commercially available and sold under various tradenames.

Unfortunately, therapeutic and cosmetic administration of botulinum toxin provides a treatment but not a cure for various conditions. Accordingly, repeated administration is necessary in order to maintain beneficial results. For example, for cosmetic applications, such as to remove frown lines, BOTOX® is typically administered every 3-6 months in order to achieve and maintain a wrinkle-free (or reduced) appearance. The body may degrade botulinum toxin and thereby destroy the biological efficacy of the material.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

The present disclosure provides the combination of colloidal silver particles and botulinum toxin. In exemplary aspects, the present disclosure provides compositions, kits, and methods of use that include both colloidal silver particles and botulinum toxin. For instance, in one aspect the present disclosure provides compositions comprising botulinum toxic and colloidal silver particles, including the following exemplary embodiments:

1) A composition comprising botulinum toxin (BTX), colloidal silver particles and water.
2) The composition of embodiment 1 wherein the BTX is botulinum type A neurotoxin.
3) The composition of embodiment 1 wherein the BTX is botulinum type B neurotoxin.
4) The composition of embodiment 1 comprising 100-600 units of BTX.
5) The composition of embodiment 1 comprising a concentration of colloidal silver of 1 to 100 ppm.
6) The composition of embodiment 1 wherein the colloidal silver is characterized by particle size, and more than 50% of the colloidal silver particles have a maximum dimension of less than 0.015 micrometers.
7) The composition of embodiment 6 wherein at least 90% of the colloidal silver particles have diameters between 0.005 micrometers and 0.015 micrometers.
8) The composition of embodiment 1 wherein the colloidal silver particles comprise metal silver of formula Ag(0) and ionic silver of a formula selected from Ag(I), Ag(II), and Ag(III).
9) The composition of embodiment 1 having a total concentration of silver of between about 5 and 40 parts per million, wherein said silver is in the form of a stable and colorless colloidal suspension of silver particles having an interior of metallic silver and an exterior surface of ionic silver oxide, wherein at least 75% of the silver particles have diameters between 0.005 micrometers and 0.015 micrometers.

In another aspect, the present disclosure provides a kit that comprises both botulinum toxin and colloidal silver particles in separate containers. For instance, the present disclosure provides the following exemplary embodiments:

10) A kit comprising a container comprising botulinum toxin (BTX) and a container comprising colloidal silver particles and water.
11) The kit of embodiment 10 further comprising a needle and syringe suitable for transferring the colloidal silver particles to the container of BTX.

In another aspect, the present disclosure provides methods of using botulinum toxin (BTX) and colloidal silver particles. For instance, the present disclosure provides the following exemplary embodiments:

12) A cosmetic treatment comprising administering botulinum toxin (BTX), colloidal silver particles and water to a subject in need thereof.
13) A medical treatment comprising administering botulinum toxin (BTX), colloidal silver particles and water to a subject in need thereof.

The details of one or more aspects and embodiments are set forth in the description below. The features illustrated or described in connection with one exemplary embodiment may be combined with the features of other embodiments. Other features, objects and advantages will be apparent from the description, and the claims.

DETAILED DESCRIPTION OF THE INVENTION

Briefly stated the present invention provides the combination of colloidal silver particles and botulinum toxin, including kits, compositions and methods of use thereof.

Colloidal Silver Particles

The terms "colloidal silver particles" or "colloidal silver" refers to particles which in whole or in part comprise silver, where the particles are colloidally suspended in an aqueous medium. The total amount of colloidal silver particles in a composition is typically between 1 and 100 ppm. In optional embodiments, the content of colloidal silver particles in the composition is about 30±5 ppm, or 25±5 ppm, or 20±5 ppm, or 15±5 ppm, or 10±5 ppm. As the particles become smaller, a given concentration of particles will represent a larger number of particles. In addition, the total surface area for a given particle concentration will increase. Therefore, particle size and range of particle size may further characterize the compositions of the present invention. In further embodiments, the present disclosure provides that more than 50% of the particles have a maximum dimension less than 0.015 micrometers; or that more than 75% of the particles have a maximum dimension less than 0.015 micrometers; or that more than 90% of the particles have a maximum dimension less than 0.02 micrometers; or that more than 75% of the particles have a minimum dimension greater than 0.005 micrometers; or that more than 90% of the particles have a minimum dimension greater than 0.005 micrometers.

The particles may optionally be characterized in terms of valence of the silver. In one embodiment, the silver particles include both silver in the zero-valent state represented as [Ag(0)], i.e., metallic silver, and a coating of silver in an ionic oxidation state selected from Ag(I), Ag(II), and Ag(III). Optionally, the particles may include silver oxide, e.g., AgO. For example, in one embodiment the particles comprise Ag(0) and AgO, where AgO is present as a coating on the particles. In one embodiment, the silver oxide in the particles may be at least partially in the form of Ag4O4, i.e., silver II oxide. In a molecule of this material two of the silver atoms are in the 1+ state (silver I) while the other two silver molecules are in the 3+ state (silver III). Under certain conditions these molecules can give rise to silver atoms in the 2+ (silver II) state. Thus, the present disclosure provides silver particles comprising metallic silver and silver oxide, the silver oxide being selected from AgO and Ag4O4.

Within optional embodiments of the invention these particles can range in size from 1 to 100 nanometers, or from 1 to 10 nanometers, or from 5 to 7 nanometers. Moreover, within preferred embodiments the particles are surrounded by a multivalent silver oxide coating comprised of Ag4O4 molecules.

Exemplary aqueous compositions comprising colloidal silver particles are described in, and may be prepared by techniques disclosed in U.S. Pat. Nos. 6,214,299; 6,743,348; 7,135,195; and 8,535,728 as well as U.S Publication No. 2011/0262556. For example, the preparation of a composition comprising colloidal silver particles may utilize an electrochemical cell comprising electrodes. The process comprises the steps of: (a) placing a silver electrode in contact with a quantity of high purity water; (b) conveying electrical current through the silver electrode to thereby separate particles of silver from said silver electrode in a manner sufficient to cause production of suspended silver particles within the water; and (c) agitating the water during said production of suspended silver particles to thereby disperse the silver particles into a more uniform concentration within said water such that a higher quantity of colloidal silver particles can be produced per batch.

As another example, the preparation of a composition comprising colloidal silver particles may comprise the steps of: (a) establishing an electrical circuit comprising a current source, and a first conductor electrically connected to said current source and a second conductor electrically connected to said current source, wherein said first conductor is disposed spaced apart from said second conductor, and wherein at least one of the conductors is made of elemental silver; (b) closing the circuit by placing the first conductor and the second conductor in communication with a fluidic resistor; (c) operating the current source to supply alternating current simultaneously to the first conductor and the second conductor such that voltage is increasing and decreasing within the first and second conductors in alternating tandem to thereby cause silver particles to separate from the first electrode and enter the fluidic resistor and become disposed in suspension within said fluidic resistor; and (d) selectively adjusting the electrodes by moving them toward the fluidic resistor to compensate for decrease in electrode length due to gradual separation of silver particles therefrom to thereby prevent arcing from occurring between the electrodes and said fluidic resistor.

Other suitable colloidal silver particles and their preparation are described in, e.g., PCT Publication No. WO 2009/009143 and US Publication No. 2010/0187091. Colloidal silver is available commercially from, e.g., American Biotech Labs of Alpine, Utah, USA.

In one embodiment, the colloidal silver particles are stable in essentially pure water without surfactants, etc. Additionally, or in another embodiment, the solution of colloidal silver particles is essentially colorless. The colloidal silver may be present in a hydrosol.

BTX

As used herein, the term "BTX" is used to generally to refer to botulinum toxin. Botulinum toxin is a neurotoxin protein naturally produced by various bacteria, e.g., Clostridium botulinum as described below. At least eight different serotypes of BTX are recognized, and they are commonly designated as A, B, C1, C2, D, E, F, and G. Exemplary sources of BTX are *C. argentinense, C. baratii, C. botulinum,* and *C. butyricum*. In one embodiment, the BTX is BTX-A. In one embodiment, the BTX is BTX-B.

Each of BTX-A and BTX-B are approved for human use by the FDA for several indications and are commercially available from several sources. For example, BOTOX® is available from Allergan Inc. Irvine, Calif., USA. DYSPORT® is available from Valeant Pharmaceuticals Int'l. Inc., Laval, Quebec, Canada. NEUROBLOC® and MYOBLOC® are both available from Solstice Neurosciences Inc. Malvern, Pa., USA. XEOMIN® is available from Merz Pharma GmbH & Co. KGaA, Frankfurt am Main, Germany.

BTX may be obtained from commercial sources as a lyophilized powder (see, e.g., U.S. Publication No. US 2014/0086900). It may be combined with water or saline at physiological pH at a suitable concentration for its intended cosmetic or medical use. BTX concentrations are generally expressed in terms of mouse units. One unit is equal to the amount of BTX that kills 50% of a group of 18- to 22-g Swiss Webster mice when injected intraperitoneally. Different BTX materials will have a different weight of BTX per unit. Indeed, different preparations of a BTX material may have a different weight of BTX per unit. BOTOX® injections of less than 100 units are usually used for cosmetic purposes and of less than 300-600 units for other purposes. The amount of aqueous solution added to the lyophilized BTX will depend on the intended purpose. 100 units commonly are reconstituted in 1-10 mL of diluent. As an example, for oculoplastic purposes 1-mL dilution per 100 units of BTX may be used. As another example, for dermatology and plastic surgery purposes, a range from 1-4 mL per 100 units may be used. As another example, 100 unit of BTX may be diluted with about 1 mL of aqueous composition comprising silver nanoparticles at a concentration of about 1 to about 50 ppm to provide a composition that may be injected into a patient to treat wrinkles such as frown lines. The aqueous phase may be gently injected into the vial of powdered BTX via syringe. The vials are typically provided by the manufacturer having a negative pressure, so that fluid is pulled into the vial upon injection. After reconstitution, the aqueous BTX composition is preferably maintained at 2-8° C. during storage.

Alternatively, the BTX may be formulated as a nanoemulsion, see, e.g., U.S. Publication Nos. 2014/0099342; and 2012/0064136.

BTX/Ag Compositions

In one embodiment, the present disclosure provides a composition comprising water, BTX and colloidal silver particles. In another embodiment, the present disclosure provides a method of making a composition comprising water, BTX and colloidal silver. These compositions may be prepared by combining reconstituted BTX with colloidal silver particles and thoroughly mixing the combination to provide a homogeneous composition. The amount or concentration of BTX in the composition should be suitable for the intended medical or cosmetic use of the composition. In order to provide the desired concentration of BTX, the lyophilized BTX may be reconstituted with less than the total amount of desired aqueous phase, and then a volume of aqueous colloidal silver particles is added to the reconstituted BTX to provide the desired concentration of BTX.

The BTX/Ag compositions, which are also referred to herein as BB, may have from 10 to 600, or from 50 to 600, or from 100 to 600, or from 10 to 400, or from 50 to 400, or from 100 to 400, or from 10 to 200, or from 50 to 200, or from 100 to 200, or about 100 units of BTX. The concentration of the silver particles based on the weight of water in which the silver particles are suspended, may range from 1 to 100 ppm, or from 1 to 50 ppm, or from 1 to 30 ppm, or from 5 to 50 ppm, or from 5 to 40 ppm, or from 5 to 30 ppm, or from 10 to 100 ppm, or from 10 to 50 ppm, or from 10 to 30 ppm. As mentioned previously, the concentration of silver in the final composition may range, for example, from 1 to 100 ppm.

Kits

In another aspect, the present disclosure provides a kit that comprises both botulinum toxin and colloidal silver particles in separate containers. For instance, the present disclosure a kit that comprises a container that holds botulinum toxin (BTX) and a container that holds colloidal silver particles and optionally also water. The kit may optionally contain further components that assist in the administration of the BTX and colloidal particles. For example, the kit may contain a syringe and needle that may be used to transfer the colloidal silver particles to the container of BTX. In addition, the kit may contain saline or aqueous buffer that may be used to reconstitute the BTX, if that BTX is in a powdered form. The kit may also include instructions for the use of the components in the kit and the administration of the BTX and colloidal silver particles to a patient.

Optionally, the kit comprises a container that comprises from 1 to 500, or 10 to 250, or about 100 units of BTX and a separate container that comprises colloidal silver at a concentration of from about 1 to 50 ppm, or about 5 to 40 ppm, or about 10 to 30 ppm. When the container that hold BTX has about 100 units of BTX then optionally the container that holds the colloidal silver has about 1 mL of water with about 1 to 50 ppm colloidal silver. The kit may optionally comprise yet another container that comprises water without colloidal silver, e.g., a buffer solution.

Methods of Use

The compositions of the present disclosure may be used for medical or cosmetic purposes. For example, they may be used for the treatment of strabismus, hemifacial spasms, cervical dystonia and blepharospasm. The compositions of the present disclosure may be used for the treatment of rhinitis, see, e.g., PCT Publication Nos. WO 2014/066916 and 2014/037531. The compositions of the present disclosure may be used for the treatment of premature ejaculation, see, e.g., WO 2014/031809. The compositions of the present invention may be used for the treatment of cerebrovascular disease, see, e.g., U.S. Publication No. 2014/0105883. The compositions of the present disclosure may be used for the treatment of migraine headache, see, e.g., PCT Publication No. WO 2013/137969. The compositions of the present disclosure may be used for the treatment of autonomic nervous system disorders, see, e.g., PCT Publication No. WO 2013/009625. The compositions of the present disclosure may be used for the treatment of esophageal spasms, see, e.g., PCT Publication No. WO 2013/009584. The compositions of the present disclosure may be used for the treatment of persistent genital arousal disorder, see, e.g., U.S. Publication No. 2012/0282241. The compositions of the present disclosure may be used for the treatment of sensory disturbance disorder, see, e.g., PCT Publication No. WO 2012/134897. The compositions of the present disclosure may be used for the treatment of a disease or condition caused by or associated with hyperactivity of muscles or exocrine glands, see, e.g., PCT Publication No. WO 2011/160826.

Accordingly, the present disclosure provides compositions that are pharmaceutical compositions comprising BTX and colloidal silver particles, where the pharmaceutical composition is sterile.

The compositions of the present disclosure may be used for cosmetic purposes, e.g., to reduce the appearance changes associated with aging, i.e., for anti-aging effect, see, e.g., PCT Publication No. WO 2011/154126. Aging is associated with the development of lines and wrinkles caused by actinic damage, gravitational effect, sleep lines, and muscular action. Mimetic facial musculature may undergo hypertrophy secondary to hyperfunctional pull. BTX injections reduce facial lines caused by hyperfunctional muscles. They also are used to contour aspects of the face such as the brows. The compositions of the present disclosure may be used for the cosmetic purposes for which BTX is used. For example, a composition of the present disclosure may be used to treat infraorbital dark circles, see, e.g., US Publication No. 2012/0115792.

The administration of a composition of the present disclosure to a subject in need of a medical or cosmetic treatment may follow standard methods for BTX administration. See, e.g., the protocols disclosed in PCT Publication No. WO 2012/103415. The subject may be a human, or the subject may be a non-human mammal or bird.

Analytical Methods

The analysis of the silver content in the compositions of this invention may be done by atomic absorption (AA), inductively coupled plasma/atomic emission (ICP/AES), or other techniques known to one of ordinary skill in the art to be sensitive to silver in the appropriate concentration range. If the particles of the silver composition are small and uniformly sized (for example, 0.01 micrometers or less), a reasonably accurate assay may be obtained by running the colloid directly by AA or ICP/AES. This is because the sample preparation for AA ionizes essentially all of the silver allowing its ready detection. If the compositions comprise particles as large as 0.2 micrometers, it is preferred to use a digestion procedure. The digestion procedure is not necessarily ideal for silver compositions that may have been manufactured or stored in contact with halides or other anionic species that may react with finely divided silver, or combined with protein or other gelatinous material.

An embodiment of the digestion procedure is as follows: (a) take a 10 ml aliquot of a thoroughly mixed or shaken silver composition to be analyzed, and place it in a clean polycarbonate bottle or other container of suitable material (generally, the bottle) with a tight fitting lid. A size of 30-100 ml is preferred; (b) with a micropipette or dropper, add 0.1 ml of nitric acid, reagent grade to the silver composition in the bottle; (c) with the lid of the bottle tightly in place, heat the composition to 80° C. with mild agitation for a time sufficient to dissolve the silver—dissolution is essentially instantaneous; (d) allow the resulting mixture to cool to room temperature with the lid in place. Shake the bottle thoroughly; (e) utilize AA, ICP/AES, or equivalent means to analyze the silver content of the composition. Preferably, one will utilize a freshly prepared standard or standards, preferably prepared according the equipment manufacturer's instructions, with appropriate dilution as needed. When reporting results, one must take into account all dilutions during preparation, including the 1% dilution caused by addition of the nitric acid.

The analysis of the physical and chemical form of the silver in the compositions may be done by time-of-flight secondary ion mass spectrometry (TOF-SIMS). The TOF-SIMS technique is suitably used as a survey tool to identify the composition of unknown samples. It is capable of quantification if the appropriate microanalytical standards are available for calibration. To perform TOF-SIMS analysis, a few drops of a silver-containing composition are evaporated to dryness on a silicon substrate at ambient temperature. The residue is analyzed by TOF-SIMS. A reference silver (II) oxide (AgO) material is analyzed by placing a few particles of the reference powder as received from the vendor on a silicon substrate, and is denoted as the reference. The time-of-flight secondary ion mass spectrometry technique (TOF-SIMS) is based on the principle of bombarding a solid sample with a pulsed, finely focused beam of primary ions, and then analyzing the secondary ions produced from the surface of the sample via a time-of-flight mass spectrograph. This analytical technique is surface sensitive, deriving its information from a layer that extends to approximately 20 to 40 Å below the surface.

Size/Morphology/Composition Analysis may be performed by any of SEM, EDS (EDAX) and TEM. In particular, the silver/water compositions may be dried and placed on an EM grid and examined in an SEM (i.e., Scanning Electron Microscope) and two different TEMs (i.e., Transmission Electron Microscopes). For example, a silver/water composition may be placed onto C-film and examined by a cryo-TEM at a temperature of about −100° C. using a power level of approximately 100 kV. The silver/water composition of the present invention was therefore substantially instantly frozen. As another example, TEM analysis may be performed in the "SAD" mode. As yet another example, an EDAX spectrum (i.e., an Energy Dispersion Spectrum or "EDS") of silver particles taken from silver/water compositions of the present invention may be used to check for metallic contaminants. In one aspect, the colloidal silver particles do not contain gold or platinum.

EXAMPLES

Background:

Botox cosmetic (Botulinum Toxin A) is commercially available in 100 unit doses. Traditionally, a container of 100 units of attenuated botulinum toxin A cosmetic is diluted with about 1 mL of an inert aqueous carrier, typically saline, and then gently agitated. An intended injection site of a patient is cleaned with isopropanol. A desired amount of this diluted botox cosmetic is injected into a patient. In the following examples, the traditional saline carrier was replaced with an aqueous suspension of nanometallic silver particles as described herein, where this active aqueous carrier had a silver concentration of either 10 ppm or 30 ppm. This silver particle-containing diluted botulinum toxin A of the present disclosure will be referred to herein for convenience as BB. The aqueous nanometallic silver suspension is commercially available from American Biotech Labs as their HYDROSOL product. In addition, the intended injection site was wiped with a sterile solution of 10 ppm HYDROSOL rather than with isopropanol. Every patient in the following examples understood the experimental nature of the treatment and signed an Informed Consent For Treatment document and a non-disclosure agreement. Each injection contained 10 units of the diluted botulinum toxin A.

A total of 1469 units of Botox diluted with silver nanoparticles ("BB") were injected into the various facial muscles of 17 different patients over a 24 month period. Patients were evaluated at the day of injection, then at 7 and 21 days post injection, then at 45 day intervals thereafter. Assessment of Botox effect was determined subjectively by the injector as indicated by: the range of motion/amount of muscle activity and presence or absence of either static or functional wrinkles.

Example 1

Patient No. 1 received 44 units of BB made from 30 ppm HYDROSOL suspension. These units were injected bilaterally around the eyes, mouth and forehead. The effect of the botox lasted for 8.5 months. The patient reported a slight stinging and discomfort at the injection sites. About 10 months after receiving the 44 units of BB, the patient received 40 units of BB made from 10 ppm HYDROSOL, where these units were injected bilaterally around the eyes and into the forehead/Procerus muscles and philtum. The patient did not report any stinging or discomfort from the injections. The effect of the botox lasted for more than 10+ months. No erythema was observed.

This patient had previously received several Botox treatments where the diluent was 0.9% Neutral Buffered Saline, in these same areas. The average length of the Botox effect from these injections was 4-5 months. Accordingly, the combination of botox and silver nanoparticles according to the claimed invention results in a significantly longer-duration botox effect compared to traditional botox injections.

Example 2

Patient No. 2 received 45 units of BB made from 30 ppm HYDROSOL suspension. These units were injected bilaterally around the eyes, mouth and forehead. The effect of the botox lasted for 7.5 months. The patient reported a slight stinging and discomfort at the injection sites. About 10 months after receiving the 45 units of BB, the patient received 42 units of BB made from 10 ppm HYDROSOL, where these units were injected bilaterally around the eyes and into the forehead. The patient did not report any stinging or discomfort from the injections. The effect of the botox lasted for 9 months.

During the five years previous to receiving injections of BB as described above, this patient had previously received many Botox treatments where the diluent was 0.9% Neutral Buffered Saline, in these same areas. The average length of the Botox effect from these injections was 4-5 months. Accordingly, the combination of botox and silver nanoparticles according to the claimed invention results in a significantly longer-duration botox effect compared to traditional botox injections.

Example 3

Patient No. 3 received 34 units of BB made from 30 ppm HYDROSOL suspension. These units were injected bilaterally around the eyes and forehead. The effect of the botox lasted for 8.5 months. The patient reported a slight stinging and discomfort at the injection sites. About 50 weeks after receiving the 34 units of BB, the patient received 50 units of BB made from 10 ppm HYDROSOL, where these units were injected bilaterally around the eyes and into the forehead. The patient reported a slight discomfort at the injection sites. The effect of the botox lasted for at least 11 months. No erythema was reported.

This patient had previously received two Botox treatments where the diluent was 0.9% Neutral Buffered Saline, in these same areas. The average length of the Botox effect from these injections was 5-6 months. Accordingly, the combination of botox and silver nanoparticles according to the claimed invention results in a significantly longer-duration botox effect compared to traditional botox injections.

Example 4

Patient No. 4 received 34 units of BB made from 10 ppm HYDROSOL suspension. These units were injected bilaterally around the eyes, forehead and the left side of the upper lip. The effect of the botox lasted for 8.5 months. The patient reported a slight stinging and discomfort at the injection sites. About 11 months after receiving the 34 units of BB, the patient received 50 units of BB made from 10 ppm HYDROSOL, where these units were injected bilaterally around the eyes and into the forehead. The patient reported a slight discomfort at the site of the injections. The effect of the botox lasted for at least 10 months.

Previous to receiving injections of BB as described above, this patient had received numerous Botox treatments where the diluent was 0.9% Neutral Buffered Saline, in these same areas. No stinging or discomfort was noted at the injection sites. The average length of the Botox effect from these injections was 5-6 months. Accordingly, the combination of botox and silver nanoparticles according to the claimed invention results in a significantly longer-duration botox effect compared to traditional botox injections.

The preceding examples demonstrate that colloidal silver may be used in conjunction with botulinum toxin A to extend the muscle relaxant efficacy of BOTOX, an exemplary botulinum toxin. In addition, these studies demonstrate that colloidal silver may be used in lieu of isopropanol to provide a sterile skin surface for injections.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An injectable composition comprising botulinum toxin (BTX), colloidal silver particles and water, wherein the composition comprises from 10±5 ppm to 30±5 ppm colloidal silver particles for every 100 units of BTX suspended in the water, and wherein the colloidal silver particles are in the form of a stable and colorless colloidal suspension of silver particles having an interior of metallic silver and an exterior surface of ionic silver oxide, wherein at least 75% of the silver particles have diameters between 0.005 micrometers and 0.015 micrometers.

2. The composition of claim 1 wherein the BTX is botulinum type A neurotoxin.

3. The composition of claim 1 wherein the BTX is botulinum type B neurotoxin.

4. The composition of claim 1 wherein at least 90% of the colloidal silver particles have diameters between 0.005 micrometers and 0.015 micrometers.

5. The composition of claim 1 wherein the colloidal silver particles comprise metal silver of formula Ag(0) and ionic silver of a formula selected from Ag(I), Ag(II), and Ag(III).

* * * * *